United States Patent
Patel

(10) Patent No.: US 6,663,240 B2
(45) Date of Patent: Dec. 16, 2003

(54) METHOD OF MANUFACTURING CUSTOMIZED INTRAOCULAR LENSES

(75) Inventor: Anilbhai S. Patel, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/146,347

(22) Filed: May 15, 2002

(65) Prior Publication Data

US 2003/0214628 A1 Nov. 20, 2003

(51) Int. Cl.$^7$ .................................................. A61B 3/00
(52) U.S. Cl. ...................... 351/200; 128/898; 351/246; 623/6.11
(58) Field of Search ................................ 351/200, 205, 351/211, 212, 246, 247; 606/4, 5; 623/4.1, 5.11, 5.12, 6.11, 6.19, 6.22, 6.27, 6.32; 128/898

(56) References Cited

U.S. PATENT DOCUMENTS

| | | |
|---|---|---|
| 5,358,520 A | 10/1994 | Patel |
| 5,366,502 A | 11/1994 | Patel |
| 5,777,719 A | 7/1998 | Williams et al. |
| 6,413,276 B1 | 7/2002 | Werblin |
| 6,543,453 B1 * | 4/2003 | Klima et al. ................ 128/898 |

FOREIGN PATENT DOCUMENTS

| | | |
|---|---|---|
| WO | WO 01/60240 | 8/2001 |
| WO | WO 02/22004 | 3/2002 |
| WO | WO 02/34158 | 5/2002 |
| WO | WO 02/051338 A1 | 7/2002 |

* cited by examiner

*Primary Examiner*—George Manuel
(74) *Attorney, Agent, or Firm*—Jeffrey S. Schira

(57) ABSTRACT

A method of manufacturing an intraocular lens that has been customized to provide optimum vision for an eye with prior corneal refractive surgery. Such a custom manufactured IOL will address not only optical correction requirements as currently met by spherical or toric-shaped IOLs, but will correct higher order optical aberrations using needed optimum customized shapes.

16 Claims, 1 Drawing Sheet

METHOD OF MANUFACTURING CUSTOMIZED INTRAOCULAR LENSES

BACKGROUND OF THE INVENTION

This invention relates generally to the field of ophthalmic lenses and, more particularly, to intraocular lenses (IOLs).

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

The power of an IOL generally is calculated using measurements of the axial length of the eye and the corneal power of the eye. The axial length is measured either by an ultrasonic A-scan device or an optical device (e.g., IOL Master sold by Zeiss Humphrey) which uses an interferometric method. The corneal power is usually measured by a keratometer. The IOL power calculation is carried out by selecting one of many mathematical formulae involving IOL-related specific constants. For example, the A-Constant for the SRK™ formula, the ACD Constant for the Binkhorst-type formula or the Surgeon Factor for the Holladay formula, etc. IOLS are typically manufactured in 0.5 diopter power increments and the surgeon implants the IOL with the power most closely corresponding with the calculated required power as per the preferred formula with clinically individualized constants developed by the surgeon for the particular IOL and the preferred formula. This method has proven to be acceptable over the years and most patients can be brought to within +/−1.00 diopters of the targeted refraction.

During the 1990s, the use of photoablative lasers to reshape the surface of the cornea (photorefractive keratectomy or PRK) or for mid-stromal photoablation (Laser-Assisted In Situ Keratomileusis or LASIK) have been approved by regulatory agencies in the U.S. and other countries. Additional corneal refractive surgical procedures are now being performed widely such as Laser-Assisted Sub-Epithelial Keratectomy or LASEK and contact or non-contact Thermal Keratoplasty or TK/CK. All of these corneal refractive surgical procedures cause an irreversible modification to the shape of the cornea in order to effect refractive changes, and if the correct refraction is not achieved by the first procedure, a second procedure or enhancement must be performed. Additionally, the longterm stability of the correction is somewhat variable because of the variability of the biological wound healing response between patients. As a result, the traditional method of calculating the required power of an IOL based on axial length and central corneal power biometric readings may not be accurate for those eyes that have undergone corneal refractive surgery. In addition, there may be higher order refractive errors in the optical system of the eye that are not adequately addressed with the current IOL power calculation methods and even if these higher order errors are recognized, the current practice of manufacturing IOLS only in discrete spherical (or in the case of toric IOLS, spherical and cylinder) power steps may not enable the surgeon to optimize the patient's vision.

One patent, U.S. Pat. No. 5,777,719 (Williams, et al.), the entire contents of which being incorporated herein by reference, describes a wavefront-based system for the custom manufacture of intraocular implants, but no specific steps in the manufacturing process are disclosed.

One published WIPO publication, International Patent Application No. PCT/US01/28425 (Publication No. WO 02/22004), the entire contents of which being incorporated herein by reference, describes a system and business model wherein wavefront measurements of the eye are taken and those measurements are used as input for a custom lens manufacturing system. While such a system may be suitable for the manufacture of some types of lenses, such a system is not practical for the manufacture of customized IOLs for several reason. The primary reason for the replacement of the natural lens is the development of a cataract. The opacity of the cataractous lens makes optical wavefront measurement of the eye difficult or impossible. Therefore, the wavefront measurement of the eye must be performed after the natural lens has been removed. Even the most advanced implantable lens manufacturing techniques require a certain amount of time, usually days, to actually make the lens because the lens must be fabricated, possible extractables removed, cleaned, sterilized and aerated. Therefore, there will be some period of time between the removal of the natural lens and the implantation of the IOL, thus requiring two separate surgeries. There are also anatomical changes to the eye that occur once the natural lens has been removed, such as capsule shrinkage, that makes it undesirable for there to be any length of time between the removal of the natural lens and the implantation of the IOL.

In addition, the refractive power of the IOL depends, in large part, to the final position of the lens in the eye. This variable is unknown until the lens is actually implanted in the eye. As a result, even the best surgeons only achieve targeted refraction within +/−1.00 diopters in 80% of their patients using current spherical or toric power IOLs for correction of only lower order refractive errors. There is little reason to assume that attempted correction of higher order refractive errors will be any more accurate.

Accordingly, a need continues to exist for an IOL that can be customized to address higher order refractive errors or changes to the cornea as a result of prior corneal refractive surgery. Such customized IOLs are needed for optimum visual outcome in such eyes.

BRIEF SUMMARY OF THE INVENTION

The present invention improves upon the prior art by providing a method of manufacturing an intraocular lens that has been customized to provide optimum vision for an eye with prior corneal refractive surgery. Such a custom manufactured IOL will address not only optical correction requirements as currently met by spherical or toric-shaped IOLs, but will correct higher order optical aberrations using needed optimum customized shapes.

The methods disclosed herein provide optimized prescriptive correction with two embodiments of an IOL. The first embodiment involves the manufacturing of IOLs of fixed shapes for optimum optical correction for a series of groups of patients, each group representing a category of prior corneal refractive surgery, including dioptric correction achieved by the prior surgery. The second embodiment involves the manufacture and implantation of a customized supplementary lens on a primary lens previously implanted in an eye with prior corneal refractive surgery. The primary lens can be similar to currently available spherical or toric-shaped IOLs or can be a custom-shaped IOL as per the first embodiment of the present invention.

Accordingly, one objective of the present invention is to provide a customized intraocular lens.

Another objective of the present invention is to provide a method of manufacturing customized intraocular lenses.

These and other advantages and objectives of the present invention will become apparent from the detailed description and claims that follow.

DETAILED DESCRIPTION OF THE INVENTION

Figure 1:
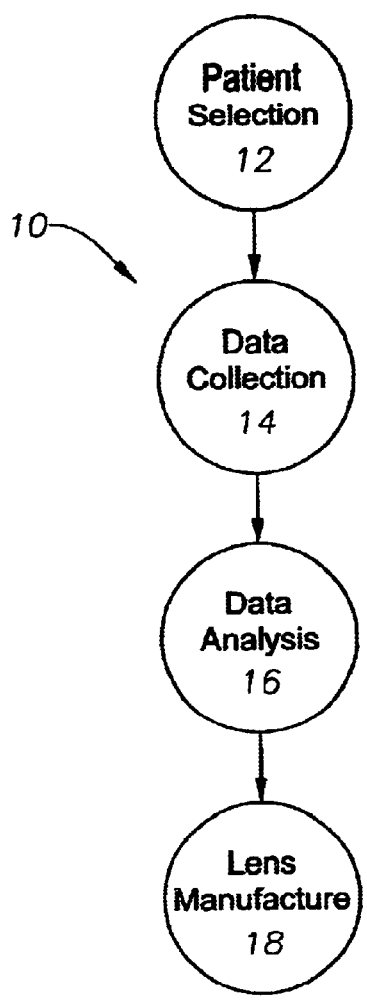
FIG. 1 is a diagram of the steps of a first embodiment of the method of the present invention.
Figure 2:
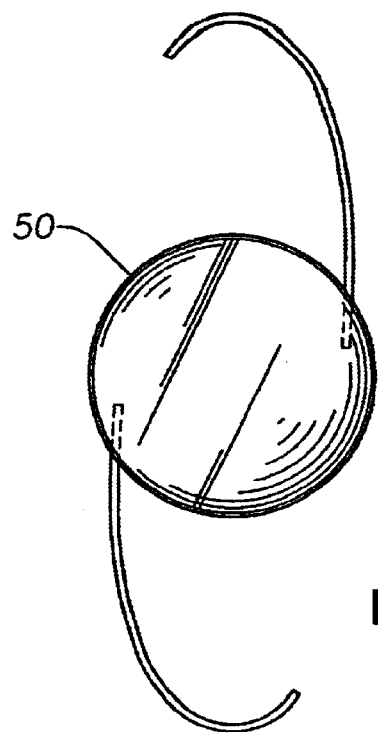
FIG. 2 is an illustration of an intraocular lens made according to the first embodiment of the present method.

As best seen in FIG. 1, method 10 of the present invention generally includes patient selection step 12. During step 12, a specific group of patients is selected having a common prior corneal refractive surgical procedure which attempted to correct a common specific refractive error within a common specific error range. A specific group of patients may be defined as consisting of those patients having previously undergone a specific type of corneal refractive surgery (e.g., PRK, LASIK, LASEK, TK, CK and others) for a correction within a specific range of refractive corrections. The correction range for myopia may be in the steps of 1 diopter of sphere up to −10 diopters of sphere with accompanying cylindrical correction for each range of spherical correction in steps of 0.5 diopters up to +5 diopters. Similarly, the correction range for hyperopia may be in 1 diopter spherical steps with accompanying 0.5 diopter cylindrical steps up to +5 diopters of sphere and +5 diopters of cylinder.

For example, the specific group of patients could be selected from a universe of patients all having undergone prior LASIK surgery during which a correction of −3D to −4D of myopic spherical with <0.5D of cylindrical refractive error was attempted. One skilled in the art will recognize that other selection criteria may also be used, and the above description is only one example.

The number of members in the selected group of patients must be large enough for statistical significance. After selecting the desired group of patients in step 12, data collection step 14 is implements. During step 14, data is collected on the shape of each eye in the group. Such data normally will include at least axial length, anterior chamber depth, corneal thickness, anterior corneal shape and posterior corneal shape. These measurements can be made by any of a variety of available diagnostic measurement devices, such as high frequency ultrasound, pachymetry, optical coherence tomography, Scheimpflug photography, corneal topography and others. During data analysis step 16, the data collected during step 14 is analyzed by an optical software based eye model for each of the specific eyes in the group of patients, such software being commercially available and well-known in the art. For each case, optimum image formation on the retina is achieved with the targeted lower order aberrations and minimized higher order aberrations by the optimum shaping of the IOL through iterative computations. This optimum IOL prescription is averaged for all eyes in the selected group of patients and is used during manufacturing step 18 to manufacture lens 50 that has been optimized for each group of patients. In this way, customized lens 50 can be manufactured in advance for a wide variety of groups of patients with prior corneal refractive surgery. IOL 50 may be manufactured in +/−0.25D or +/−0.50D steps within each group of patients.

Figure 3:
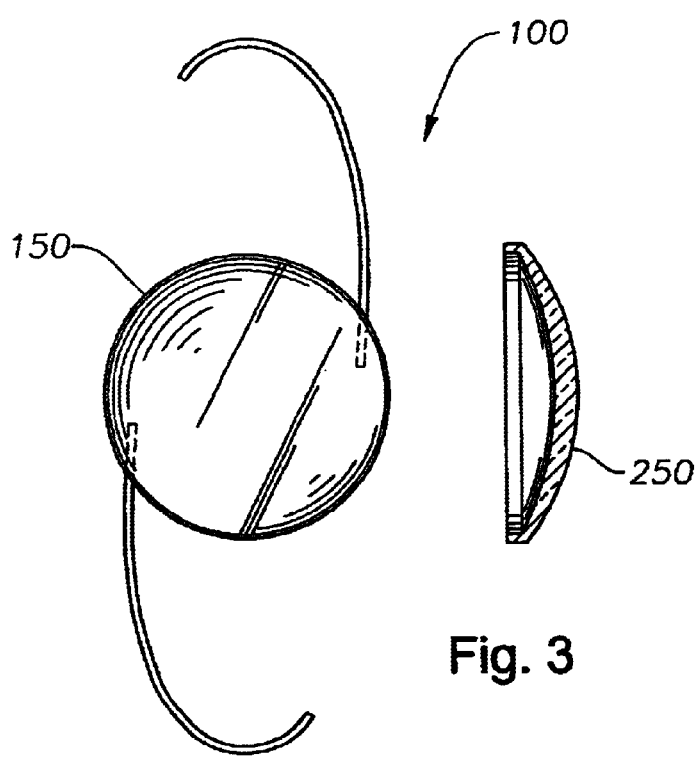
FIG. 3 is an illustrations of an intraocular lens system made according to the second embodiment of the present method.

Alternatively, as shown in FIG. 3, lens system 100 may consist of primary lens 150 and supplementary lens 250. Primary lens 150 may be implanted in an eye in a conventional manner using appropriate mathematical formulae as described above. Following implantation of primary lens 150, data collection step 14 and data analysis step 16 is performed on the postoperative eye in which primary lens 150 is implanted. As a result of data analysis step 16, any residual lower and high order optical aberrations are analyzed and an optimized prescription for customized supplementary lens 250 is computed using an optical software based eye model in order to achieve targeted lower order aberrations and minimized higher order aberrations. Supplementary lens 250 is manufactured according to the optimized prescription and supplementary lens 250 is implanted in the eye and attached to primary lens 150 in the manner described in U.S. Pat. Nos. 5,358,520 and 5,366,502, the entire contents of which being incorporated herein by reference. Such optimized prescriptions may be calculated on an individualized basis, or based on data analysis for a grouping of patients.

Lenses 50, 150 and 250 can be made of any conventional material, such as thermoplastic, silicone, a hydrogel or a soft acrylic, such materials and manufacturing methods being well-known in the art.

This description is given for purposes of illustration and explanation. It will be apparent to those skilled in the relevant art that changes and modifications may be made to the invention described above without departing from its scope or spirit.

I claim:

1. A method of manufacturing a customized intraocular lens, comprising the steps of:
   a) selecting a group of patients having undergone a common prior corneal refractive surgical procedure for correcting a similar refractive error;
   b) collecting data on the shape of each eye in the group of patients;
   c) analyzing the data collected on the shape of each eye in the group of patients;
   d) calculating an optimized prescription for an intraocular lens for each group of patients; and
   e) manufacturing the intraocular lens according to the optimized prescription.

2. The method of claim 1 wherein the common prior corneal refractive surgical procedure is LASIK.

3. The method of claim 1 wherein the common prior corneal refractive surgical procedure is PRK.

4. The method of claim 1 wherein the common prior corneal refractive surgical procedure is LASEK.

5. The method of claim 1 wherein the common prior corneal refractive surgical procedure is TK.

6. The method of claim 1 wherein the corn meal refractive surgical procedure is CK.

7. The method of claim 1 wherein the data collected on the shape of each eye in the group of patients includes at least axial length, anterior chamber depth, corneal thickness, anterior corneal shape and posterior corneal shape.

8. A method of manufacturing a customized intraocular lens system, comprising the steps of:
   a) implanting a primary intraocular lens in an eye of a patient;
   b) collecting data on the eye postoperatively following implantation of the primary intraocular lens;
   c) analyzing the data collected on the post operative eye following implantation of the primary intraocular lens; and
   d) calculating an optimized prescription necessary to achieve a targeted lower order and minimized higher order aberrations in the eye for a supplementary intraocular lens;
   e) manufacturing the supplementary intraocular lens according to the optimized prescription; and
   f) implanting the supplementary intraocular lens in the eye.

9. The method of claim 8 wherein the data collected on the eye includes at least axial length, anterior chamber depth, corneal thickness, anterior corneal shape and posterior corneal shape.

10. A method of manufacturing, a customized intraocular lens system, comprising the steps of:
   a) implanting a primary intraocular lens in an eye of a patient, the eye having previously undergone a corneal refractive surgical procedure;
   b) collecting data on the eye postoperatively following implantation of the primary intraocular lens;
   c) analyzing the data collected on the post operative eye following implantation of the primary intraocular lens; and
   d) calculating an optimized prescription necessary to achieve a targeted lower order and minimized higher order aberrations in the eye for a supplementary intraocular lens;
   e) manufacturing the supplementary intraocular lens according to the optimized prescription; and
   f) implanting the supplementary intraocular lens in the eye.

11. The method of claim 10 wherein the data collected on the eye includes at least axial length, anterior chamber depth, corneal thickness, anterior corneal shape and posterior corneal shape.

12. The method of claim 10 wherein the previous corneal refractive surgical procedure is LASIK.

13. The method of claim 10 wherein the previous corneal refractive surgical procedure is PRK.

14. The method of claim 10 wherein the previous corneal refractive surgical procedure is LASEK.

15. The method of claim 10 wherein the previous corneal refractive surgical procedure is TK.

16. The method of claim 10 wherein the previous corneal refractive surgical procedure is CK.

* * * * *

UNITED STATES PATENT AND TRADEMARK OFFICE
CERTIFICATE OF CORRECTION

PATENT NO. : 6,663,240 B2
DATED : December 16, 2003
INVENTOR(S) : Anilbhai S. Patel It is certified that error appears in the above-identified patent and that said Letters Patent is hereby corrected as shown below:

<u>Column 4,</u>
Line 62, "corn meal" should read -- common prior --

Signed and Sealed this

Twenty-fifth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,663,240 B2
DATED : December 16, 2003
INVENTOR(S) : Anilbhai S. Patel It is certified that error appears in the above-identified patent and that said Letters Patent is hereby corrected as shown below:

Column 3,
Line 52, "implements" should read -- implemented --

Column 4,
Line 14, "step 16 is" should read -- step 16 are --
Line 31, "as thermoplastic, silicone," should read -- as a thermoplastic, a silicone --

Signed and Sealed this

First Day of February, 2005

JON W. DUDAS
*Director of the United States Patent and Trademark Office*